United States Patent
Stevanato et al.

(10) Patent No.: US 12,416,586 B2
(45) Date of Patent: Sep. 16, 2025

(54) SYSTEM AND PROCESS FOR DETERMINING THE WATER EQUIVALENT CONTENT OF A SNOWPACK

(71) Applicant: FINAPP S.r.l., San Pietro in Cariano (IT)

(72) Inventors: Luca Stevanato, Abano Terme (IT); Marcello Lunardon, Verona (IT); Sandra Moretto, Padua (IT); Giancarlo Nebbia, Cinto Euganeo (IT)

(73) Assignee: FINAPP S.r.l., San Pietro in Cariano (VR) (IT)

( * ) Notice: Subject to any disclaimer, the term of this patent is extended or adjusted under 35 U.S.C. 154(b) by 174 days.

(21) Appl. No.: 18/567,903

(22) PCT Filed: Jun. 9, 2022

(86) PCT No.: PCT/IB2022/055369
§ 371 (c)(1),
(2) Date: Dec. 7, 2023

(87) PCT Pub. No.: WO2022/259197
PCT Pub. Date: Dec. 15, 2022

(65) Prior Publication Data
US 2024/0272092 A1    Aug. 15, 2024

(30) Foreign Application Priority Data

Jun. 11, 2021   (IT) .................. 102021000015287

(51) Int. Cl.
*G01N 23/02*   (2006.01)
*G01N 33/18*   (2006.01)

(52) U.S. Cl.
CPC ....... *G01N 23/025* (2013.01); *G01N 33/1873* (2024.05); *G01N 2223/102* (2013.01);
(Continued)

(58) Field of Classification Search
CPC ............ G01N 23/025; G01N 33/1873; G01N 2223/102; G01N 2223/107;
(Continued)

(56) References Cited

U.S. PATENT DOCUMENTS 3,665,180 A * 5/1972 Guillot ...................... G06F 7/62
378/53
4,992,667 A * 2/1991 Abelentsev ............ G01N 23/09
250/390.05
(Continued)

FOREIGN PATENT DOCUMENTS

WO    2020141406 A1    7/2020

OTHER PUBLICATIONS

Luca, S., "Local high-energy particles measurements for detecting primary cosmic-ray variations: application for soil moisture estimation", Oct. 8, 2020, 6th International Cosmos Workshop, Heidelberg University, p. 21, XP055894079 (Year: 2020).*
(Continued)

*Primary Examiner* — Blake C Riddick
(74) *Attorney, Agent, or Firm* — Florek & Endres PLLC

(57) ABSTRACT

The present invention relates to a system (S) and a process for determining the water equivalent content of a snowpack (Snow Water Equivalent—SWE).

10 Claims, 3 Drawing Sheets

(52) U.S. Cl.
CPC . *G01N 2223/107* (2013.01); *G01N 2223/205* (2013.01); *G01N 2223/302* (2013.01); *G01N 2223/505* (2013.01)

(58) Field of Classification Search
CPC ....... G01N 2223/205; G01N 2223/302; G01N 2223/505
See application file for complete search history.

(56) References Cited

U.S. PATENT DOCUMENTS

| | | | | |
|---|---|---|---|---|
| 5,594,250 | A * | 1/1997 | Condreva | G01T 1/178 250/361 R |
| 11,092,716 | B1 * | 8/2021 | Pust | G01S 19/14 |
| 2002/0194922 | A1 * | 12/2002 | Schaefer | G01L 1/20 73/720 |
| 2003/0080199 | A1 | 5/2003 | Condreva | |
| 2008/0087837 | A1 | 4/2008 | Desilets et al. | |
| 2008/0164407 | A1 * | 7/2008 | Choquette | G01T 1/20 250/262 |
| 2011/0073771 | A1 * | 3/2011 | Frolik | G01V 5/02 702/188 |
| 2011/0298647 | A1 * | 12/2011 | Long | G01S 13/9027 342/22 |
| 2014/0366648 | A1 * | 12/2014 | Christian | G01W 1/14 73/862.621 |
| 2018/0259447 | A1 * | 9/2018 | Johnson | E02D 1/022 |
| 2019/0383967 | A1 * | 12/2019 | Polebitski | G01K 11/22 |
| 2021/0041398 | A1 * | 2/2021 | Van Wyk | G01N 29/04 |
| 2021/0156810 | A1 | 5/2021 | Botto et al. | |
| 2022/0091052 | A1 * | 3/2022 | Stevanato | G01N 23/09 |

OTHER PUBLICATIONS

Martin, Hazel, "International Search Report and Written Opinion of the International Searching Authority for PCT/IB2022/055369," European Patent Office, Aug. 19, 2022.

Stevanato Luca, "Local high-energy particles measurements for detecting primary cosmic-ray variations: application for soil moisture estimation", Oct. 8, 2020 (Oct. 8, 2020), p. 21-21, 6th International Cosmos Workshop, Heidelberg University, Oct. 8-10, 2020, Retrieved from the Internet: URL: https://www.uni-potsdam.de/fileadmin/projects/cosmicsense/6th_International_COSMOS_Workshop_Booklet.pdf.

* cited by examiner

SYSTEM AND PROCESS FOR DETERMINING THE WATER EQUIVALENT CONTENT OF A SNOWPACK

FIELD OF APPLICATION

The present invention relates to a system (S) and a process for determining the water equivalent content of a snowpack (Snow Water Equivalent—SWE).

STATE OF THE ART

As is well known, snowmelt in mountainous areas is often of great importance in terms of freshwater supply, as it represents a water reserve that has a gradual release capacity. Furthermore, the evolution and amount of seasonal snow accumulation in high mountain regions is a key parameter in many climate-related research fields, such as glaciology, hydrology and various climate change studies. Changes in snow accumulation in mountain areas caused by climate change are expected to have a major impact on water supply, hydropower production and tourism.

However, traditional snow sampling techniques are invasive, labour-intensive and have other disadvantages such as low repetition frequency and objective difficulty in covering large areas. In this context, snow condition data from ground measurements and remote sensing systems are increasingly being used for snow hydrology applications.

There are numerous automated in situ measurements to determine snow thickness (snow layer—SD) or snow water content, understood as Snow Water Equivalent (SWE, mm), but these are generally limited and have high sensitivity to local anomalies. Furthermore, it is difficult to obtain accurate measurements with high spatial and temporal resolution in high mountain regions.

In particular, the estimation of the SWE (i.e. the thickness of the water layer resulting from the melting of a volume of snow) provides information on the total amount of solid-state water stored in the snow and its spatial distribution. Estimating the SWE allows the average snowpack height to be derived from snow density and water density. This approach is generally based on the integration of automatic and manual measurements and/or satellite data feeding numerical models. Snow pillows are one of the most widely used tools in this context. Specifically, they are load cells that are used to measure the weight of snow deposited on their surface. In fact, the hydrostatic pressure within the pillow is proportional to the weight of snow deposited on it. This pressure is measured by means of a liquid-float gauge recorder or transducer and allows the water equivalent of the snowpack to be determined continuously. However, such measurements present several problems, including poor accuracy due to the possible formation of ice layers (causing a "bridging effect" on the pillow) and/or temperature variations and/or wind.

Space-based remote sensing products would overcome these limitations and fulfil most of the above requirements. However, the high maintenance costs associated with such techniques are a major obstacle. Recently, promising measurement techniques with low maintenance costs have been suggested for monitoring SWE based on acoustic sensors, gamma-ray scintillators, GPS interferometric reflectometry or cosmic ray neutron sensors (CRNS). Among these, the use of CRNS for the determination of SWE, known since the late 1970s (Kodama et al, '*An application of cosmic-ray neutron measurements to the determination of the snow-water equivalent*', J. Hydrol., 41, 85-92, 1979), is based on the attenuation of natural radiation by snow. In particular, when natural cosmic rays reach the ground, they are attenuated by the hydrogen atoms contained in the water that makes up the snowpack. In fact, it is known that the production of neutron energy between epithermal and slow (0.5 eV-50 keV) is regularly influenced by the presence of hydrogen, which, in turn, is directly related to water content. This information, suitably processed by mathematical models, lends itself to meeting the need for real-time knowledge of the water availability condition of cultivated land, snow cover and vegetation. However, although this technique has already widely demonstrated its potential for monitoring soil moisture in a wide range of environments and applications, empirical knowledge of its use for measuring and monitoring snowpack is still limited to shallow snowpacks with rather uniform evolution. There are currently two different methodologies based on the use of CRNS for measuring and monitoring a snowpack. The first methodology involves the use of such sensors placed at a certain height above the snowpack, while in the second methodology they are installed at ground level, where they may possibly be entirely covered by snow.

As described by the scientific article "*Continuous monitoring of snowpack dynamics in alpine terrain by aboveground neutron sensing*" (Schattan et al., Water Resource Research, Volume 53, Issue 5, May 2017, Pages 3615-3634), the use of CRNS arranged above the snowpack offers several advantages, including good accuracy in measuring SWE, the possibility of integrating a signal over a large area, and the fact that the measurement is not disturbed by moisture in the soil for snowpacks at least 30 mm tall during winter periods. However, this methodology has some disadvantages, including the impossibility of making reliable measurements for snowpacks above 600 mm SWE and the need to calibrate the sensor during summer periods or in the absence of snow due to the moisture present in the soil.

The use of CRNS at ground level, on the other hand, allows SWE measurements to be made for snowpacks up to approximately 2,000 mm, however, this methodology has important disadvantages, including the limited range (which is in the order of about ten square metres), high measurement variability due to the moisture present in the soil, and the objective difficulty of acquiring and/or transmitting data for sensors installed deeply beneath snowpacks ("*Continuous and autonomous snow water equivalent measurements by a cosmic ray sensor on an alpine glacier*", Gugerli et al, The Cryosphere, 13, 3413-3434, 2019).

Another disadvantage of the two methodologies is that they are unable to provide information on the homogeneity of snow thickness in a given area of interest when used individually. In fact, it is pointed out that snow thickness can vary in a given area due to various factors, such as wind (which can lead to snow accumulation in certain areas) and rough land. Consequently, the use of such methodologies does not allow for complete and detailed characterisation of the area of interest.

In addition, both methodologies are generally based on sensors measuring ambient neutrons from incident cosmic ray flux data provided by some research centres. However, the use of these data is not very precise because they depend on certain factors such as geographical location, time of year and local weather conditions. Indeed, it must be considered that such data can be collected several hundred kilometres away and their usability is not guaranteed in any way, as they are made available at the discretion of the research centre. Consequently, in certain cases, such data may be of little use and/or of little significance. Systems have recently been developed in which the measurement of ambient neutron flux is normalized by measuring the flux of incident cosmic rays. For example, the technical solution proposed by international patent application WO 2020/141406 A1 describes a device for measuring the water content of soil, vegetation and/or a snowpack in which the measurement of incident cosmic ray flux is used to correct the measurement of ambient neutron flux. These systems therefore represent a definite advantage over the previously known technique, which used cosmic ray flux values provided by research centres. However, the use of such systems above the snowpack or at ground level still has the drawbacks described above.

OBJECT OF THE INVENTION

The purpose of the present invention is thus to provide a system (S) and a process for determining the equivalent water content of a snowpack that is particularly advantageous compared to the known art.

Specifically, the subject matter of the present invention is a system (S) for determining the equivalent water content of a snowpack comprising:
  a first device (D1) to be positioned at a height (h) with respect to the maximum expected thickness (x) of said snowpack, said first device (D1) comprising at least a first module (1a) adapted to measure a flux of electrons and muons from the interactions of the primary cosmic rays with the upper layers of the atmosphere and a control unit (1c);
  a second device (D2) to be positioned at ground level and possibly covered by said snowpack, said second device (D2) comprising at least a first module (2a) adapted to measure a flux of cosmic electrons and muons incident on the ground;
wherein said control unit (1c) is connected to said at least a first module (1a) of said first device (D1) and to said at least a first module (2a) of said second device (D2) and is adapted to process the measurements of the flux of electrons and muons from the interactions of the primary cosmic rays with the upper layers of the atmosphere made by said at least a first module (1a) of said first device (D1) and the measurements of the flux of cosmic electrons and muons incident on the ground made by said at least a first module (2a) of said second device (D2) to determine the water equivalent content of said snowpack (V1).

The subject matter of the present invention is also a process for determining the equivalent water content of a snowpack comprising the steps of:
  positioning at a height (h) with respect to the maximum expected thickness (x) of said snowpack a first device (D1) comprising at least a first module (1a) adapted to measure a flux of electrons and muons from the interactions of the primary cosmic rays with the upper layers of the atmosphere and a control unit (1c);
  positioning at ground level and possibly buried in said snowpack a second device (D2) comprising at least a first module (2a) adapted to measure the flux of electrons and cosmic muons incident on the ground;
  processing the measurements made by said at least a first module (1a) of said first device (D1) and by said at least a first module (2a) of said second device (D2) by means of said control unit (1c) to obtain a determination of the water equivalent content of said snowpack (V1);
wherein the determination of the water equivalent content of said snowpack (V1) is obtained from the measurement of the flux of cosmic electrons and muons incident on the ground carried out by the at least a first module (2a) of said second device (D2) normalized with respect to the measurement of the flux of electrons and muons from the interactions of the primary cosmic rays with the upper layers of the atmosphere carried out by the at least a first module (1a) of said first device (D1).

DESCRIPTION OF THE DRAWINGS

Further features and advantages of the present invention can be more readily understood from the following description of its preferred and non-limiting examples of embodiments, wherein.

DETAILED DESCRIPTION OF THE INVENTION

It has surprisingly been found that the system (S) and the process according to the present invention can solve some of the drawbacks of using CRNS positioned above the snowpack or at ground level.

In particular, the system (S) and the process according to the present invention make it possible to:
  eliminate the variability due to humidity that is observed in the measurement of ambient neutrons;
  reduce measurement errors due to the use of cosmic ray incident flux data provided by third parties to normalize ambient neutron flux measurements;
  reduce the costs of using CRNS while maintaining the quality of the data provided.

These advantages derive mainly from the fact that the system (S) and the process of the present invention are based on the measurement of the muon and electronic component of secondary cosmic rays to determine the equivalent water content of the snowpack. Indeed, the inventors have surprisingly found that it is possible to use flux measurements of the muon and electron component of secondary cosmic rays instead of the neutron component.

Specifically, the system (S) and process according to the present invention are based on the phenomenon of muon and electron flux attenuation observed when muons and electrons pass through the snowpack. This attenuation phenomenon is directly proportional to the thickness of the snowpack. Accordingly, the measurement of the flux of cosmic electrons and muons incident on the ground carried out by the at least one first module (2a) comprised in the second device (D2) can be related to the measurement of the flux of electrons and muons from the interactions of primary cosmic rays with the upper layers of the atmosphere carried out by the at least one first module (1a) comprised in the first device (D1) to determine the equivalent water content of the snowpack. In fact, the flux of cosmic electrons and muons incident on the ground measured by the at least one first module (2a) of the second device (D2) turns out to be attenuated by the snowpack, while the flux of electrons and muons from primary cosmic ray interactions with the upper layers of the atmosphere carried out by the at least one first module (1a) of the first device (D1) turns out to be unperturbed.

It should also be noted that the measurement of the muon and electron component of secondary cosmic rays is not disturbed by the moisture present in the soil and, consequently, the determination of the equivalent water content of the snowpack is not subject to variability.

The measurement of the muon and electron component of secondary cosmic rays according to the following invention makes it possible to determine the equivalent water content for snowpacks up to SWE values of 2,000 mm and with an action range of about ten square metres.

These are therefore comparable operating conditions to the use of CRNS at ground level.

Figure 1:
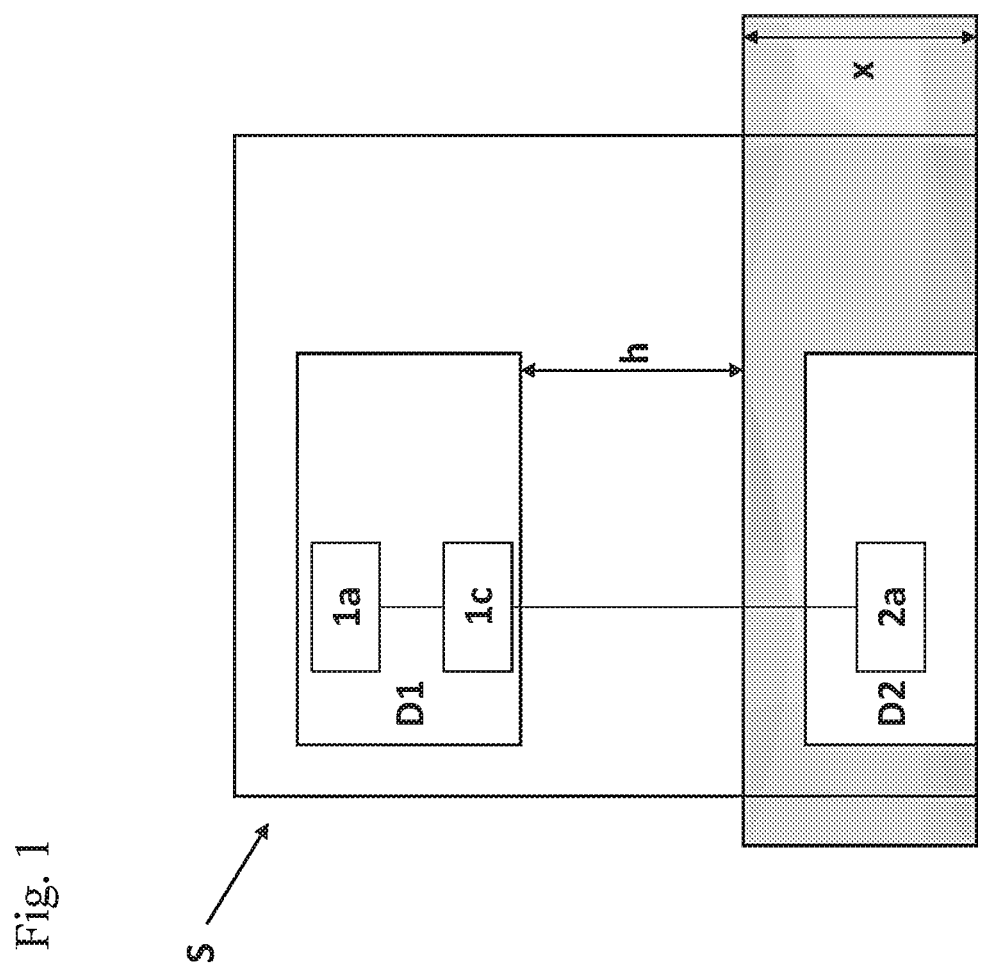
FIG. 1 shows in schematic form a system as a whole, denoted by the reference S, for determining the equivalent water content of the snowpack according to the present invention.

FIG. 1 shows the system (S) as a whole according to the present invention in schematic form. This system, as mentioned, comprises:

- a first device (D1) to be positioned at a height (h) with respect to the maximum expected thickness (x) of said snowpack, said first device (D1) comprising at least a first module (1a) adapted to measure a flux of electrons and muons from the interactions of the primary cosmic rays with the upper layers of the atmosphere and a control unit (1c);
- a second device (D2) to be positioned at ground level and possibly covered by said snowpack, said second device (D2) comprising at least a first module (2a) adapted to measure a flux of cosmic electrons and muons incident on the ground. Said control unit (1c) is connected to said at least a first module (1a) of said first device (D1) and to said at least a first module (2a) of said second device (D2) and is adapted to process the measurements of the flux of electrons and muons from the interactions of the primary cosmic rays with the upper layers of the atmosphere made by said at least a first module (1a) of said first device (D1) and the measurements of the flux of electrons and cosmic muons incident on the ground made by said at least a first module (2a) of said second device (D2) to determine the water equivalent content of said snowpack (V1).

In accordance with an embodiment, in that system (S):
said first device (D1) comprises at least a second module (1b) connected to said control unit (1c) and adapted to measure an ambient neutron flux;
the at least a first module (1a) of said first device (D1) is also adapted to measure a flux of high-energy neutrons and protons from the interactions of the primary cosmic rays with the upper layers of the atmosphere;
said control unit (1c) is adapted to process the measurements of the flux of ambient neutrons made by said at least second module (1b) of said first device (D1) and the measurements of the flux of high-energy neutrons, protons, electrons and muons from the interactions of the primary cosmic rays with the upper layers of the atmosphere made by said at least a first module (1a) of said first device (D1) to provide a further value of water equivalent content of said snowpack (V2).

Figure 2:
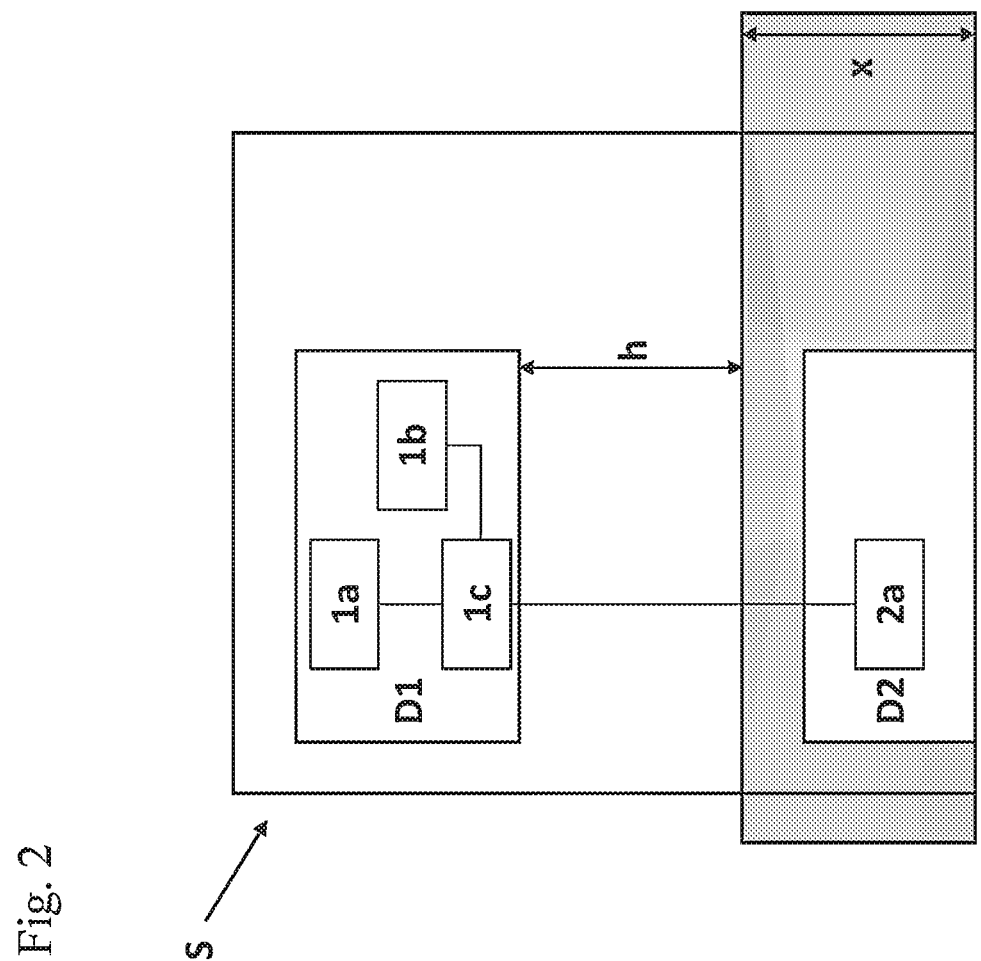
FIG. 2 shows in schematic form an alternative embodiment of said system (S)

A non-limiting example of this embodiment is illustrated in FIG. 2. Specifically, the normalization of the measurements of the flux of ambient neutrons made by said at least second module (1b) of said first device (D1) according to the measurements of the flux of high-energy neutrons, protons, electrons and muons from the interactions of the primary cosmic rays with the upper layers of the atmosphere made by said at least a first module (1a) of said first device (D1) by means of said control unit (1c) allows to provide a further value of water equivalent content of said snowpack (V2).

The determination of a second value of the equivalent water content of the snowpack (V2) obtained from the measurement of the environmental neutron flux normalized with respect to the measurement of the flux of incident cosmic rays (i.e. high-energy neutrons, protons, electrons and muons from the interactions of primary cosmic rays with the upper layers of the atmosphere) allows in cases where the snowpack has an SWE value of 600 mm or less (i.e. within the range of values where the use of CRNS above the snowpack is reliable), to determine the equivalent water content even in the case of malfunctions of the second device (D2). Moreover, since this second value (V2) refers to a larger area than the one obtained by measuring the muon and electronic component (V1), it is possible, from the comparison of the two values (V1) and (V2) determined in this way, to obtain information on the homogeneity of the snowpack thickness in the perimeter of interest. In fact, the more similar the value of the equivalent water content of the snowpack determined from the measurement of the ambient neutron flux (V2) is to the value of the equivalent water content of the snowpack determined from the measurement of the muon and electronic component (V1), the more homogeneous the snowpack in the area concerned is.

Figure 3:
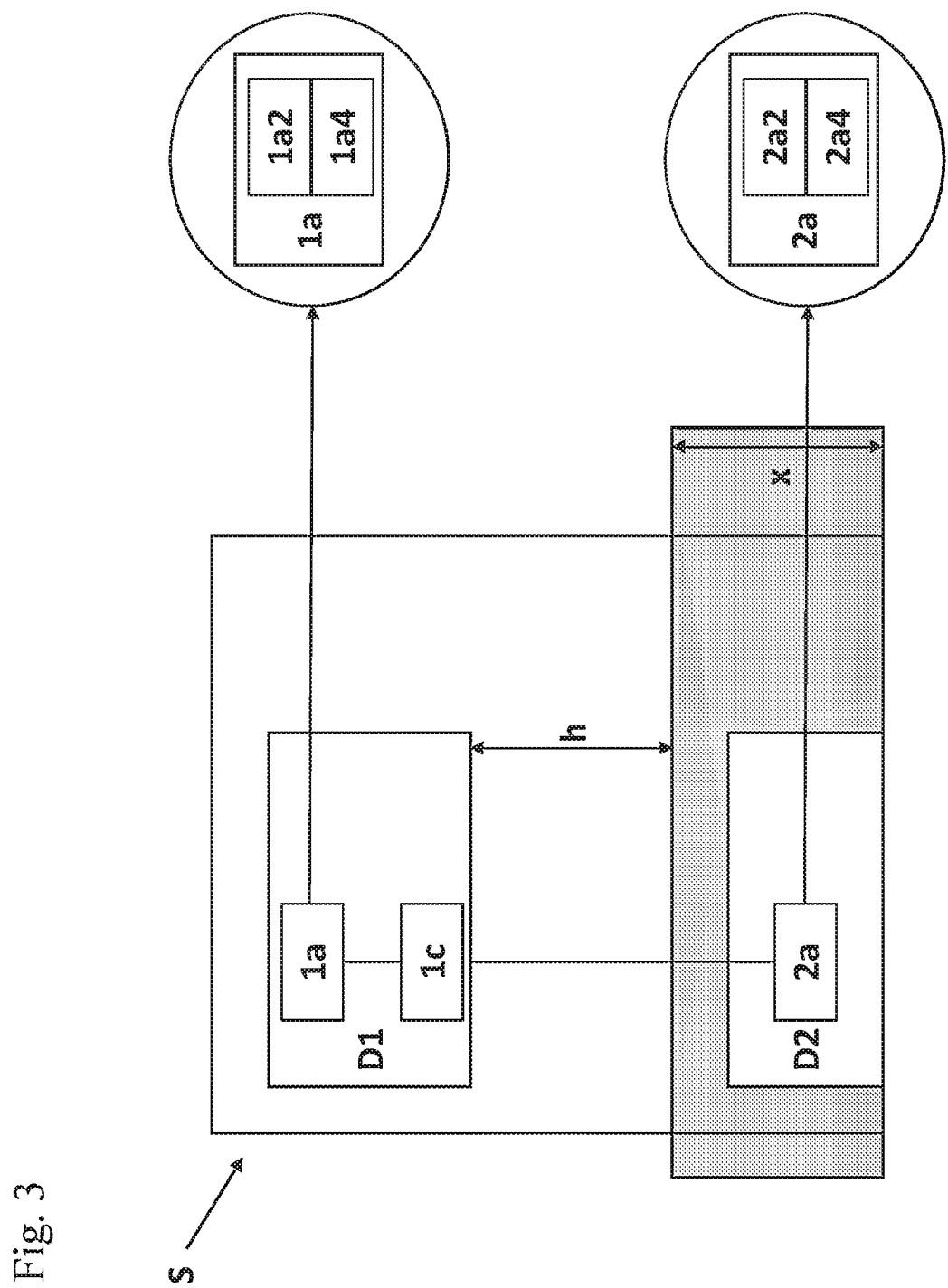
FIG. 3 shows in schematic form a further alternative embodiment of said system (S).

In a preferred embodiment, said at least a first module (1a) of said first device (D1) and/or said at least a first module (2a) of said second device (D2) comprise/comprises a scintillator (1a2/2a2) and at least one light meter (1a4/2a4) adapted to measure the light emitted by said scintillator (1a2/2a2). A non-limiting example of this embodiment is illustrated in FIG. 3.

As is well known, a scintillator is a material capable of emitting pulses of light when it is crossed by high-energy photons or charged particles, and thus also by the incident flux of cosmic rays. For the measurement of the incident cosmic ray flux through the detection of muons, electrons and possibly also high-energy neutrons [E>2 MeV] and protons in the case of the scintillator (1a2) of the first module (1a) of the first device (D1), the use of a plastic scintillator was found to be particularly advantageous.

The at least one first-module light meter (1a4/2a4) suitable for measuring the light emitted by said scintillator (1a2/2a2) may be a silicon photomultiplier, also known as SiPM (Silicon PhotoMultiplier). As is well known, silicon photomultipliers are produced directly from a layered silicon structure on which arrays of microcells are arranged on a silicon substrate. Each microcell is a single-photon Avalanche Photodiode, or APD. SiPM-type photomultipliers have very low volume, weight, consumption and price compared to conventional vacuum-tube photomultipliers. They are also much more mechanically robust and do not require the high voltage supply (around 1,000 V) typical of photomultiplier tubes.

In one embodiment, said at least second module (1b) possibly comprised in said first device (D1) may comprise a polyethylene coating suitable for moderating the energy of ambient neutrons. The polyethylene of which the coating is composed can be high or low density, and can vary in thickness between 1 and 10 cm.

In a further embodiment, said at least second module (1b) possibly comprised in said first device (D1) may comprise a first slab and a second slab made at least partially with scintillator; and a light guide interposed between the first slab and the second slab. The first sheet and the second sheet may comprise scintillator crystals, such as ZnS(Ag), in a silicone-based matrix, which provides greater mechanical strength of the scintillator sheets and better heat resistance than other types of matrix. The light guide can be made as a WLS solid plate, or as a WLS fibre-optic bundle. WLS refers to a material that, when hit by a certain wavelength, emits a one of a different wavelength.

Said at least second module (1*b*) which may be comprised in said first device (D1) may additionally comprise at least one second module light meter suitable for measuring the light transmitted by the light guide. Said second module light meter can be a silicon photomultiplier (SiPM). Advantageously, said at least second module (1*b*) possibly comprised in said first device (D1) may comprise two second-module light meters arranged on opposite sides of the light guide so as to drastically reduce the electronic noise of the SiPM even at low thresholds.

These devices (D1) and (D2) may include a power supply with at least one solar panel and a buffer battery and/or be equipped with a remote connection module that allows the data processed to be sent externally, via a wifi or equivalent connection, or GSM, to an external server.

Advantageously, signal training, digitizing and processing, power management and sending the processed data externally and/or between the two devices (D1) and (D2) can be performed with a dedicated ultra-low power (<0.5 W) board, further reducing the size and cost of the solar panel and buffer battery, which is particularly useful when using the device in the open field.

In a preferred embodiment, said first device (D1) is positioned at a height (h) comprised between 3 and 4 metres above the expected maximum thickness (x) of said snowpack.

The advantages that can be achieved with the system (S) and the process according to the present invention are therefore now apparent.

The system (S) and the process according to the present invention can be used for example for:
- nivo/glaciological research: monitoring of the water content in the nivo-glacial basin; this data is interesting to monitor especially in spring to find out the water availability and to monitor any sudden floods and/or avalanches caused by sudden melting of the snowpack;
- hydrological research: solid-state water stored in snow represents a water reserve that has a gradual release capacity and is at the same time a factor to be monitored in the hydrogeological control and warning chain;
- meteorological research: snowpack monitoring can help the development of automatic models useful for short-term weather forecasting;
- energy research: knowing water availability can be useful for optimizing the energy production capacity of a hydroelectric basin;
- climatological monitoring: by monitoring the snowpack, changes in snow accumulation in mountain areas caused by climate change can be measured.

To the embodiments described above, the skilled person may, in order to meet specific requirements, make modifications and or substitutions of described elements with equivalent elements, without thereby departing from the scope of the appended claims.

The invention claimed is:

1. A system for determining the water equivalent content of a snowpack comprising:
a first device configured to be positioned at a height with respect to the maximum expected thickness of said snowpack, said first device comprising a first device first module adapted to measure a flux of electrons and muons from the interactions of the primary cosmic rays with the upper layers of the atmosphere and a control unit;
a second device configured to be positioned at ground level and possibly covered by said snowpack, said second device comprising a second device first module adapted to measure a flux of cosmic electrons and muons incident on the ground;
wherein said control unit is connected to said a first device first module and to said second device first module and is adapted to process the measurements of the flux of electrons and muons from the interactions of the primary cosmic rays with the upper layers of the atmosphere made by said a first device first module and the measurements of the flux of cosmic electrons and muons incident on the ground made by said second device first module to determine the water equivalent content of said snowpack.

2. The system according to claim 1, wherein:
said first device comprises a first device second module connected to said control unit and configured to measure an ambient neutron flux;
the first device first module is also configured to measure a flux of high-energy neutrons and protons from the interactions of the primary cosmic rays with the upper layers of the atmosphere;
said control unit is configured to process the measurements of the flux of ambient neutrons made by said first device second module and the measurements of the flux of high-energy neutrons, protons, electrons and muons from the interactions of the primary cosmic rays with the upper layers of the atmosphere made by said first device first module to provide a further value of water equivalent content of said snowpack.

3. The system according to claim 2, wherein said first device second module comprises a polyethylene coating adapted to moderate the energy of the ambient neutrons.

4. The system according to claim 1, wherein said first device first module and/or said second device first module comprise/comprises a scintillator and a light meter configured to measure the light emitted by said scintillator.

5. The system according to claim 4, wherein said scintillator is a plastic scintillator.

6. The system according to claim 4, wherein said light meter configured to measure the light emitted by said scintillator is a silicon photomultiplier.

7. A process for determining the water equivalent content of a snowpack comprising the steps of:
positioning at a height with respect to the maximum expected thickness of said snowpack a first device comprising a first device first module configured to measure a flux of electrons and muons from the interactions of primary cosmic rays with upper layers of the atmosphere and a control unit;
positioning at ground level and possibly buried in said snowpack a second device comprising a second device first module configured to measure the flux of cosmic electrons and muons incident on the ground;
processing the measurements made by said first device first module and by said second device first module by means of said control unit to obtain a determination of the water equivalent content of said snowpack;
wherein the determination of the water equivalent content of said snowpack is obtained from the measurement of the flux of cosmic electrons and muons incident on the ground carried out by the second device first module normalised with respect to the measurement of the flux of electrons and muons from interactions of the primary cosmic rays with the upper layers of the atmosphere carried out by the first device first module.

8. The process according to claim 7, wherein:

said snowpack has a value of water equivalent content equal to or lower than 600;

said first device comprises a first device second module connected to said control unit and configured to measure an ambient neutron flux;

the first device first module is also adapted to measure a flux of high-energy neutrons and protons from the interactions of primary cosmic rays with upper layers of the atmosphere;

said control unit is configured to process the measurements made by said first device second module;

the normalisation of the measurements of the flux of ambient neutrons made by said first device second module according to the measurements of the flux of high-energy neutrons, protons, electrons and muons from the interactions of the primary cosmic rays with the upper layers of the atmosphere made by said first device first module obtained by means of said control unit allows to provide a further value of water equivalent content of said snowpack.

9. The process according to claim 8, comprising a further step of comparing the value of water equivalent content of the snowpack determined from the measurement of the flux of cosmic electrons and muons incident on the ground with the further value of water equivalent content of the snowpack determined from the measurement of the flux of high-energy neutrons in order to obtain information on the homogeneity of the thickness of the snowpack in a given area of interest.

10. The process according to claim 7, wherein said first device is positioned at a height of between 3 and 4 metres with respect to the maximum expected thickness of said snowpack.

* * * * *